United States Patent [19]

Nachman

[11] Patent Number: 5,714,150
[45] Date of Patent: Feb. 3, 1998

[54] METHOD FOR PRODUCING EXTRACT OF OLIVE LEAVES

[76] Inventor: Leslie Nachman, 650 Whitney Ranch Dr., Apt. 3811, Henderson, Nev. 89014

[21] Appl. No.: 780,448

[22] Filed: Jan. 8, 1997

[51] Int. Cl.$^6$ ................................................ A61K 35/78
[52] U.S. Cl. ................................................ 424/195.1
[58] Field of Search ........................................ 424/195.1

[56] References Cited

FOREIGN PATENT DOCUMENTS

| | | |
|---|---|---|
| 2507477 | 12/1982 | France . |
| 1066603 | 1/1984 | U.S.S.R. . |
| 1736501 | 5/1992 | U.S.S.R. . |

*Primary Examiner*—Jean C. Witz
*Attorney, Agent, or Firm*—Dennison, Meserole, Pollack & Scheiner

[57] ABSTRACT

A method for preparing an olive leaf extract and the extract prepared thereby. The leaves are covered with an aqueous alcohol solution which remains in contact with the leaves for at least 4 hours and is then drained. This process is repeated at least two more times, and the drained extracts are combined, concentrated by distillation under vacuum, and dried by spray drying or oven drying under vacuum, to obtain a powder containing about 30–40% by weight oleuropein. The steps of the extraction are conducted at a temperature of about 20° to 88° C.

10 Claims, No Drawings

METHOD FOR PRODUCING EXTRACT OF OLIVE LEAVES

BACKGROUND OF THE INVENTION

The invention relates to an olive leaf extract known as oleuropein with valuable medicinal properties.

Oleuropein is a bitter glucoside found in olives and the roots, leaves and bark of the olive tree, Olea europaea. Medicinal use of this extract dates back to the early 1800s when it was used in liquid form as a treatment for malarial infections. Oleuropein undergoes mild acid hydrolysis to form elenolic acid, this process being similar to an enzyme based hydrolysis of the compound which takes place in the human body.

Calcium elenolate was reported to have in vitro antiviral activity in an article by Renis, "In Vitro Antiviral Activity of Calcium Elenolate," *Antimicrobial Agents and Chemotherapy* —1969, pages 167–172. In this article, calcium elenolate was reported to have activity against a wide variety of viruses, with the greatest activity under alkaline conditions (pH 7.5).

However, when incubation was carried out with amino acids prior to incubation with virus, losses in virucidal activity were detected, especially in the presence of glycine, lysine, cysteine and histidine, and to a lesser extent with other amino acids.

In view of these results, it would be expected that oleuropein would not be an effective antiviral agent in-vivo.

More recently, oleuropein has been found to be effective, in-vitro, against Salmonella enteritidis ("Inhibition of Salmonella enteritidis by oleuropein in broth and in a model foodsystem," *Lett Appl Microbiol* 20(2):120–4, Feb. 1995), and enterotoxin B ("The effect of the olive phenolic compound, oleuropein, on growth and enterotoxin B production," *J Appl Bacteriol* 74(3):253–9, Mar. 1993). In addition, oleuropein has been found to protect low density lipoprotein from oxidation (*Life Sci* 55(24):1965–71, 1994) and to inhibit platelet aggregation (*Thromb Res* 78(2):151–60, Apr. 15, 1995).

In view of the many potential medical uses of oleuropein, it would be very useful to produce a form of oleuropein which is not inactivated in the presence of amino acids found throughout the human body.

SUMMARY OF THE INVENTION

Applicants have now discovered that the loss of activity of oleuropein administered in vivo is based on the stereochemistry of the oleuropein, causing it to bind to proteins in the blood.

It is therefore an object of the invention to provide a method for extracting oleuropein in a form which retains medicinal activity in vivo.

It is a further object of the invention to provide oleuropein in a form which undergoes hydrolysis in vivo to produce elenolic acid which retains its antiviral activity, and which does not bind to proteins in the blood.

To achieve these and other objects, the invention is directed to a method for extracting oleuropein from olive leaves comprising the steps of treating olive leaves with an alcohol and water solution to produce an alcoholic extract, draining the alcohol and water solution from the olive leaves, treating the olive leaves with fresh alcohol and water solution at least two more times, combining the alcoholic extracts produced, and distilling the combined extracts under vacuum at a temperature of about 20° to 88° C. to produce a concentrated extract having a solids content of about 30 to 40%. The concentrated extract can then be spray dried or oven dried under vacuum to produce a dry powder extract comprising approximately 30–40% by weight oleuropein.

Importantly, the above process steps must be conducted at a temperature no greater than about 88° C., since destruction of the glucoside is thought to occur at higher temperatures.

While not wishing to be held to any particular theory, Applicants believe that by conducting a plurality of low temperature alcoholic extractions followed by a low temperature distillation, the resultant oleuropein contains a high proportion of R-oleuropein as compared with L-oleuropein, the R-oleuropein not binding to amino acids in the human body, and therefore remaining active in vivo. The invention is therefore also directed to an alcoholic extract of olive leaves comprising oleuropein which is predominantly (at least 50% by weight) R-oleuropein.

The alcoholic solution used to treat the olive leaves should contain at least 25% by weight alcohol, and preferably comprises 60–75% by weight alcohol with the ratio of leaves to alcohol being approximately 1 kilogram to 3.8 liters (1 gallon). Preferably, 3 to 4 covers of the solvent are used for a full extraction, each extraction lasting at least 4 hours at 70–88° C., or at least 24 hours at room temperature (20° C.). At room temperature, each extraction may last up to about 48 hours.

In order to maximize the extraction, leaves should be selected from the tree Olea europaea, and should be tested in advance to confirm the presence of oleuropein in an amount of at least 0.30% by weight. Testing is done by standard thin layer chromatography and high pressure liquid chromatography methods. The preferred extractants for oleuropein are the lower alkanols, especially methanol, ethanol, isopropanol or a mixture thereof, and most preferably ethanol in a concentration of 70% by weight. Each extracted cover should be tested to determine its oleuropein content, and the number of covers can be adjusted to maximize extraction, although 3 or 4 covers will be used in most cases. After concentration of the extracts, the oleuropein content and solids content can be determined. Then, the contents can be adjusted so that the correct oleuropein content is obtained in the powder after drying, preferably 35% by weight.

EXAMPLE

Leaves of the tree Olea europaea are tested for oleuropein content using thin layer chromatography and high pressure liquid chromatography, and found to have an oleuropein content of approximately 0.30%. Approximately 1 kilogram of leaves is covered with 3.8 liters of 70% ethanol solution in water, and the leaves remain covered at 20° C. for 48 hours. At the end of the 48 hour period, the alcohol is drained and another 3.8 liter portion of 70% ethanol is used to cover the leaves. This procedure is repeated twice more, and after the fourth cover, all extracts are combined and distilled under vacuum at about 70° C. to produce a concentrated alcoholic solution containing about 30 to 40% solids. The solution is spray dried at a temperature under 70° C. to obtain a dry powder extract containing about 35 weight percent oleuropein.

What is claimed is:

1. A method for extracting oleuropein from olive leaves comprising the steps of:

covering olive leaves with an extractant consisting essentially of an aqueous alcohol solution containing at least 25% by weight alcohol;

contacting the olive leaves with the extractant for a period of at least about 4 hours;

draining the extractant from the olive leaves;

adding a fresh quantity of said extractant to said olive leaves for a period of at least about 4 hours, and draining said fresh portion of extractant;

adding at least one further fresh portion of said extractant to said olive leaves for a period of at least about 4 hours, and draining said fresh portion of extractant;

combining said portions of drained extractant and distilling under vacuum to achieve a concentrate containing about 30 to 40% solids by weight; and drying said concentrate to obtain a particulate extract containing about 30 to 40% by weight oleuropein.

said steps taking place at a temperature of about 20° to 88° C.

2. The process of claim 1, wherein said drying is spray drying.

3. The process of claim 1, wherein said drying is oven drying under vacuum.

4. The process of claim 1, wherein said alcohol is methanol, ethanol, isopropanol, or a mixture thereof.

5. The process claim 1, wherein said extractant consists essentially of about 60 to 75% by weight ethanol in water.

6. The process of claim 1, wherein said extractant is added to said olive leaves in an amount of approximately 3.78 liters of extractant for each kilogram of olive leaves.

7. The process claim 1, wherein said olive leaves remain in contact with said extractant for a period of about 24 to 48 hours at about 20° C.

8. The process claim 1, wherein said olive leaves remain in contact with said extractant for a period of about 4 hours at about 70° to 88° C.

9. The process of claim 1, wherein said olive leaves contain at least 0.30% by weight oleuropein.

10. The process of claim 1, wherein said particulate extract consists essentially of oleuropein in the form of R-oleuropein.

* * * * *